United States Patent [19]
Reedy et al.

[11] 3,983,148
[45] Sept. 28, 1976

[54] PROCESS FOR PRODUCING CYCLIC SILOXANES

[75] Inventors: James Dale Reedy, Williamstown; Harold D. Furbee, Sistersville, both of W. Va.

[73] Assignee: Union Carbide Corporation, New York, N.Y.

[22] Filed: Aug. 29, 1975

[21] Appl. No.: 608,986

[52] U.S. Cl. .......................................... 260/448.2 E
[51] Int. Cl.² .......................................... C07F 7/08
[58] Field of Search .............................. 260/448.2 E

[56] References Cited
UNITED STATES PATENTS

| | | | |
|---|---|---|---|
| 2,769,829 | 11/1956 | Dobay | 260/448.2 E |
| 2,769,830 | 11/1956 | Dobay | 260/448.2 E |
| 3,432,538 | 3/1969 | Curry | 260/448.2 E |
| 3,489,782 | 1/1970 | Pruvost et al. | 260/448.2 E |
| 3,627,805 | 12/1971 | Thomas et al. | 260/448.2 E |
| 3,839,388 | 10/1974 | Nitzsche et al. | 260/448.2 E |

*Primary Examiner*—Paul F. Shaver
*Attorney, Agent, or Firm*—Reynold J. Finnegan

[57] ABSTRACT

Process for producing cyclic siloxanes by hydrolysis and condensation, the improvement comprising carrying out the process in the presence of a cationic surface active agent.

13 Claims, No Drawings

PROCESS FOR PRODUCING CYCLIC SILOXANES

BACKGROUND OF THE INVENTION

This invention relates to an improved hydrolysis and condensation process for preparing cyclic siloxane compounds. More particularly this invention relates to a process for preparing cyclic siloxanes by hydrolysis and condensation of a hydrolyzable organosilicon compound, the improvement which comprises increasing the yield of said cyclic siloxanes by hydrolyzing and condensing said organosilicon compound in the presence of a cationic surface active agent, said agent being essentially soluble only in the aqueous phase of said process.

The hydrolysis and condensation of hydrolyzable organosilicon compounds, e.g. dichlorodimethylsilane to produce cyclic siloxane compounds, e.g. dimethylsiloxane trimers, tetramers, pentamers, etc., is a conventional process that is well known in the art, as seen e.g. by U.S. Pat. No. 2,905,703 and German Pat. No. 888,851. Heretofore, it has been found that cyclic siloxane product yields of about 50 percent can be obtained by carrying out the hydrolysis and condensation process at low temperatures and employing a strong mineral acid, e.g. HCl, $H_2SO_4$ and $H_3PO_4$, along with large quantities of water. Higher cyclic product yields are obviously desirable for in addition to the obvious reasons for obtaining high yields, the formation of high concentrations of cyclic siloxanes will give the manufacturer a greater processing latitude. For example, following hydrolysis and condensation it is necessary to separate the siloxane product phase and aqueous phase. As the viscosity of the siloxane product phase increases, it becomes increasingly difficult to obtain a clean separation. An increased cyclic siloxane product content decreases the viscosity of the siloxane product phase, thereby allowing easier separation from the aqueous phase. Of course, as is understood, the siloxane product phase in addition to the desired cyclic siloxanes, also contains unreacted hydrolyzable and hydroxy end-blocked linear siloxanes. Such hydrolyzable linear siloxanes are generally neutralized with basic water solutions or repeated washings which must also be separated from the cyclic siloxanes product. Because such neutralization can lead to additional viscosity increases due to condensation reactions this second separation is generally more difficult than the first, hence the need for a low viscosity cyclic siloxane product is obvious. Further, in certain production operations low yields of dimethyl cyclic siloxane products are often depolymerized to yield additional cyclic siloxanes; a higher concentration of initial cyclic products may negate the need for depolymerization in some applications.

It is known that cyclic siloxane product yields can be increased by the use of water-miscible solvents. However, large amounts of solvents are normally required and such reduces the pot yield of cyclic product in proportion to the amount of solvent employed. Moreover, the preferred solvents, e.g. para-dioxane and tetrahydrofuran, are generally soluble in both the aqueous and siloxane phases of the process and any solvent present in the cyclic siloxane product must be removed when pure siloxanes are desired thereby requiring additional procedural steps and adding to the expense of the process.

It has now been discovered that high cyclic siloxane product yields can be obtained which can easily be separated from the aqueous phase by employing the improved hydrolysis and condensation process of this invention.

SUMMARY OF THE INVENTION

Thus, it is an object of this invention to provide an improved hydrolysis and condensation process for producing a high yield of cyclic siloxane compounds. Other objects and advantages of this invention will become readily apparent from the following description and claims.

More specifically this invention can be described as an improved process for preparing cyclic siloxane compounds, said process consisting essentially of the hydrolysis and condensation of a hydrolyzable organosilicon compound, the improvement comprising increasing the yield of said cyclic siloxane compounds by hydrolyzing and condensing said organosilicon compound in the presence of a cationic surface active agent, said agent being essentially soluble only in the aqueous phase of said process, wherein the concentration of the cationic surface active agent in said aqueous phase is from about 0.01 to about 10 weight percent, wherein said cationic surface active agent is selected from the class consisting of a salt of a protonated amine, a quaternary ammonium salt, a salt of a protonated carboxylic acid, a salt of a protonated alcohol, a salt of a protonated nitrile, a salt of a protonated sulfoxide, a salt of a protonated mercaptan, a quaternary phosphonium salt, and a salt of a protonated phosphine, wherein the cation of each salt contains from 5 to 30 carbon atoms, and wherein the anion of each salt is selected from the group consisting of halide, sulfate, and phosphate anions.

It is to be understood of course that the above process and appended claims read on employing a single ingredient of the type specified or any of the various combinations of ingredient mixtures possible.

DESCRIPTION OF THE PREFERRED EMBODIMENTS

Any hydrolyzable organosilicon compound, as well as mixtures thereof, heretofore employed in a conventional hydrolysis and condensation process for preparing cyclic siloxane compounds can be employed as the starting material of the process of the instant invention. Such hydrolyzable organosilicon compounds, as well as methods for their manufacture are well known in the art.

Among the more preferred hydrolyzable organosilicon compounds useful as the starting materials in the process of this invention that may be mentioned are hydrolyzable silanes and low molecular weight hydrolyzable organosiloxanes and organosilylamines. Illustrative of such silanes include those of the formula

wherein R represents a radical selected from the class consisting of hydrogen and a monovalent hydrocarbon radical, $n$ has a value of 0 to 3 preferably 2, and X is a hydrolyzable group. Illustrative of such low molecular weigh organosiloxanes include those of the formula

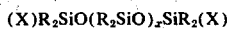

wherein R and X are the same as defined above and $x$ has a value of 0 to 3, preferably 0 to 2. Illustrative of such low molecular weight organosilylamines include those of the formula

wherein R, X and $x$ are the same as defined above. Of course it is understood that each R and each X group in a given silicon compound need not be identical.

Illustrative of the monovalent hydrocarbon groups that are represented by R above are alkyl groups (such as methyl, ethyl, propyl, isopropyl, butyl, pentyl, hexyl, octyl, decyl, dodecyl, octadecyl, eicosyl, and the like); aryl groups (such as phenyl, naphthyl, and the like); alkenyl groups (such as vinyl, allyl and the like); aralkyl groups (such as tolyl, xylyl, and the like); and cycloalkyl groups (such as cyclohexyl, and the like). If desired, such monovalent hydrocarbon groups can contain substituents such as halide atoms, e.g. trifluoromethyl, alkoxide radicals, e.g. lower alkoxy groups having 1 to 4 carbon atoms and the like, so long as they do not adversely effect the desired result and the hydrolysis and condensation reaction. Preferably said hydrocabon radicals contain from 1 to 20 carbon atoms, while alkyl and phenyl radicals are the most preferred especially lower alkyl radicals having from 1 to 4 carbon atoms and most especially methyl.

Illustrative of the hydrolyzable groups that are represented by X above are halogen radicals, e.g. chlorine, bromine, iodine and fluorine, preferably chlorine; alkoxy radicals, preferably lower alkoxy radicals 1 to 4 carbon atoms, especially methoxy; acyloxy radicals, preferably lower acyloxy radicals having from 2 to 5 carbon atoms, especially acetoxy; and amino radicals of the formula -NR'R² wherein R' represents hydrogen or a monovalent radical and R² represents a monovalent hydrocarbon radical. Illustrative monovalent hydrocarbon radicals represented by R' and R² are the same as those defined above for R, and preferably are lower alkyl having from 1 to 4 carbon atoms, especially methyl, and phenyl radicals.

The preferred hydrolyzable organosilicon starting materials are the silane compounds defined above, especially dichlorosilanes. Specific hydrolyzable silanes that may be mentioned include dichlorodimethylsilane, dichloromethylsilane, dichloromethylphenylsilane, dichlorodiphenylsilane, diethoxydimethylsilane, diacetoxydimethylsilane, bis(dimethylamino)dimethylsilane, and the like.

Specific hydrolyzable siloxanes that may be mentioned include 1,5-dichlorohexamethyltrisiloxane, 1,5-di(n-octylamino)hexamethyltrisiloxane, and the like.

Specific hydrolyzable silylamines that may be mentioned include 1,3 bis(n-octylamino) 1,1,3,3-tetramethyldisilazane, and the like.

Of course it is understood that in addition to employing a single starting material, mixtures of two or more different hydrolyzable organosilicon compounds can be employed if desired depending upon he cyclic siloxane product desired. For example, hydrolysis and condensation of $(CH_3)_2SiCl_2$ produces homopolymeric dimethylcyclic siloxanes having $(CH_3)_2$ SiO units, while cohydrolysis and condensation of $(CH_3)_2SiCl_2$ and $CH_3HSiCl_2$ (dichloromethylsilane) produces copolymeric cyclic siloxanes having $(CH_3)_2SiO$ and $CH_3HSiO$ units. It is of course obvious that monofunctional hydrolyzable silanes cannot be employed alone and require the presence of a multifunctional hydrolyzable silane to produce cyclic siloxanes. It is to be also understod that the hydrolyzable organosilicon starting material of this invention can include if desired minor amounts of any of the conventional end-blocking materials, such as chlorotrimethylsilane, hexamethyldisiloxane, and the like, as well as other conventional additives, including solvents, heretofore employed in conventional hydrolysis and condensation processes used to prepare cyclic siloxane compounds. The most preferred starting materials of this invention are dichlorodimethylsilane, mixtures of dichlorodimethylsilane and dichloromethylsilane, and mixtures of dichlorodimethylsilane, dichloromethylsilane and chlorotrimethylsilane.

It has now been discovered that the yield of cyclic siloxanes can be significantly increased by hydrolyzing and condensing the organosilicon starting material in the presence of a cationic surface active agent that is essentially soluble only in the aqueous phase of the process.

Illustrative cationic surface active agents that may be employed in this invention are salts of a protonated amine such as $RNH_3^+$, $R_2NH_2^+$, and $R_3NH^+$; quaternary ammonium salts such as $R_4N^+$; salts of a protonated carboxylic acid such as $RC^+(OH)_2$; salts of a protonated alcohol such as $R(OH)^+_2$; salts of a protonated nitrile $RCNH^+$; salts of a protonated sulfoxide such as $R_2S^+OH$; salts of protonated mercaptan such as $RSH^+_2$; quaternary phosphonium salts such as $R_4P^+$; and salts of a protonated phosphine such as $R_3PH^+$; wherein R is a radical selected from the group consisting of hydrogen and a monovalent hydrocarbon radical as defined above, wherein the cation of each salt contains from 5 to 30 carbon atoms, and wherein the anion of each salt is selected from the group consisting of halide sulfate and phosphate anions. Of course it is understood that each R group in a given compound need not be identical. Preferably the cation of each salt contains from 6 to 18 carbon atoms and the anion is chloride. Such cationic surface active agents and/or methods for their manufacture are well known.

Illustrative examples of such salts of protonated amines are e.g., n-$C_5H_{11}N^+H_3.Cl^-$, n-$c_6H_{13}N^+H_3.Cl^-$, n-$C_8H_{17}$-N$^+$H$_3$. Cl$^-$, n-$C_{18}H_{37}N^+H_3.Cl^-$, (n-$C_4H_9)_2N^+H_2.Cl^-$, (n-$C_4H_9)_3N^+H.Cl^-$, n-$C_{10}H_{21}N^+H_3.Cl^-$, and the like.

Illustrative examples of such quaternary ammonium salts are e.g. tetra-n-butylammonium chloride, tetra-n-butylammonium iodide, n-cetyltrimethylammonium chloride, and the like.

Illustrative examples of such salts of protonated carboxylic acids are e.g., n-$C_4H_9C^+(OH)_2.Cl^-$, n-$C_5H_{11}C^+(OH)_2.Cl^-$, and the like.

Illustrative examples of such salts of protonated alcohols are e.g., t-$C_5H_{11}O^+H_2.Cl^-$, n-$C_6H_{13}O^+H_2.Cl^-$, n-$C_5H_{11}O^+H_2.Cl^-$, and the like.

Illustrative examples of such salts of protonated nitriles are e.g. n-$C_4H_9CN^+H.Cl^-$, and the like.

Illustrative examples of such salts of protonated sulfoxides are e.g., n-$C_8H_{17}S^+(OH)CH_3.Cl^-$, and the like.

Illustrative examples of such salts of protonated mercaptans are e.g. n-$C_6H_{13}SH_2$. Cl$^-$, n-$C_7H_{15}S^+H_2.Cl^-$, and the like.

Illustrative examples of such quaternary phosphonium salts are e.g., $(n-C_4H_9)_4P^+.Cl^-$, $(n-C_5H_{11})_4P^+.Cl^-$, and the like.

Illustrative examples of such salts of protonated phosphines are e.g., $(n-C_4H_9)_3P^+H.Cl^-$, $(n-C_5H_{11})_3P^+H.Cl^-$, and the like.

The preferred cationic surface active agents of this invention are the salts of protonated amines, most preferably the salts of protonated primary amines of the formula $RN^+H_3$ wherein R is a monovalent hydrocarbon radical having 6 to 10 carbon atoms; the salts of protonated secondary amines of the formula $R_2N^+H_2$ wherein R is a monovalent hydrocarbon radical wherein the sum number of the carbon atoms of both R radicals of the secondary amine ranges from 8 to 14; and the salts of protonated tertiary amines of the formula $R_3N^+H$ wherein R is a monovalent hydrocarbon radical wherein the sum number of the carbon atoms of all three R radicals of the tertiary amine ranges from 9 to 18. More preferably each R radical of said protonated amines is an n-alkyl radical. The most preferred of all the cationic surface active agents is n-octylammonium chloride, $(n-C_8H_{17}N^+H_3.Cl^-)$.

Of course, it is understood that in addition to employing a single cationic surface active agent, mixtures of two or more different cationic surface active agents can be employed if desired. The cationic surface active agents employable in this invention are those that are essentially soluble only in the aqueous phase of the hydrolysis and condensation process, i.e. those that have a greater solubility in the aqueous phase (aqueous medium) than in the organosilicon phase (organosilicon starting material-siloxane product medium) of the process. In addition the cation of the cationic surface active agents employable in this invention contain from 5 to 30 carbon atoms. Cationic surface active agents which are more soluble in the organosilicon phase than in the aqueous phase of the process are unacceptable since they may contaminate the siloxane product and adversely affect product quality. Likewise, unacceptable cationic surface active agents include those containing less than 5 carbon atoms in the cation of the agent such as ethylammonium chloride, trimethylammonium chloride, the chloride salt of protonated acetonitrile, the chloride salt of protonated acetic acid, and the like. Moreover, as a general rule cationic surface active agents having shorter hydrocarbon chain lengths than the preferred agents employed herein give diminishing yields of cyclic siloxane product, those having longer hydrocarbon chain lengths give good yields but tend to form semi-stable emulsions which make it difficult to separate the siloxane product and aqueous phase. Thus, it is obvious that a hydrophile-lipophile balance is an important consideration in choosing the cationic surface active agent to be employed. As a general rule the most preferred cationic surface active agents are those which have the best solubility in the aqueous phase and which best may be cleanly separated along with the aqueous phase from the siloxane product phase in the shortest period of time. For example, n-octylammonium chloride has a solubility of less than 150 parts per million in the organosilicon phase of the process.

Of course, it is to be further understood that there is also an optimum concentration of cationic surface active agent for formation of the maximum yield of cyclic siloxanes in a hydrolysis and condensation process. The concentration of the cationic surface active agent in the aqueous phase of the process of this invention can range from about 0.01 to about 10 weight percent with the preferred concentration being about 0.5 to about 2 weight percent. Of course just as there is an optimum cationic surface active agent concentration for forming the maximum yield of total cyclic siloxane product compounds, there is also an optimum level for maximizing any individual cyclic siloxane product compound. Generally increasing the concentration of cationic surface active agent present in the process increases the amount of higher molecular weight cyclic siloxanes. However, in doing so it should be noted that the net effect may be to reduce the total cyclic content of siloxane product. In any event, the cationic surface active agent should never be present in the process in sufficient quantities so as to be the reaction solvent.

Further, it is understood that while individual cationic surface active agents may perform differently toward the same organosilicon starting material as well as toward different organosilicon starting materials, the optimum result desired as well as the optimum reaction conditions for producing same with regard to employing any particular cationic surface active agent is well within the routine experimentation of one having average skill in the art.

The hydrolysis and condensation process of this invention can be provided with a cationic surface active agent by either of two methods. For instance, a preformed surface active agent, e.g., tetrabutylammonium chloride, bromide or iodide, and the like, can be added to the aqueous phase employed in the hydrolysis and condensation process, which aqueous phase can contain or be free of mineral acid. Alternatively and more preferably the cationic surface active agent can be formed in situ by employing an aqueous phase that contains a strong mineral acid such as HCl, $H_2SO_4$, and $H_3PO_4$ and the corresponding precursor of the cationic surface active agent desired. Under such hydrolysis and condensation conditions the precursor is protonated to form, in situ the corresponding protonated salt, i.e. desired cationic surface active agent. For example, an aqueous phase containing hydrochloric acid and n-octylamine produces the corresponding n-octylammonium chloride salt. Thus, it is obvious that amines such as $RNH_2$, $R_2NH$ and $R_3N$, carboxylic acids such as RCOOH, alcohols such as ROH, nitriles such as RCN, sulfoxides such as $R_2SO$, mercaptans such as RSH, and phosphines such as $R_3P$, wherein R is the same as defined above, are the precursors which can be added to the aqueous-acid medium of the hydrolysis and condensation process of this invention to form in situ the corresponding above defined protonated amine, carboxylic acid, alcohol, nitrile, sulfoxide, sulfide, and phosphine salts. Of course it is to be understood that since mixtures of two or more different cationic surface active agents can be provided in the process of this invention if desired, likewise the aqueous-acid medium when employed can contain mixtures of two or more different precursors as defined above, if desired.

Such precursor compounds and/or methods for their preparation are well known and of course it is obvious that the preferred precursors are those which correspond to the preferred cationic surface active agents defined above such as primary amines of the formula $RNH_2$, secondary amines of the formula $R_2NH$, and tertiary amines of the formula $R_3N$, which correspond to the above defined protonated primary, secondary and tertiary amines. Likewise the amounts of precursor and mineral acid employed in the in situ type process is matched to that amount of cationic surface active agent desired for a given hydrolysis and condensation process. For example, it is generally preferred that the concentration of hydrogen chloride in water ranges from 10 to 40 percent by weight while the preferred optimum concentration of n-octylamine in the aqueous-acid medium is from 0.5 to 2 percent by weight.

The other reaction conditions of the hydrolysis and condensation process of this invention are not narrowly critical and correspond to those of known hydrolysis and condensation reactions. The reaction temperature may range from −15°C. to 150°C., although the preferred temperature range is from 0°C. to 110°C. Pressure is not critical and the reaction can be run at sub-atmospheric, atmospheric and super-atmospheric pressures. The preferred pressures are atmospheric and above. Upper pressure levels may be restricted by equipment limitations. The hydrolysis and condensation process of this invention can be run continuously or batch-wise. On a production scale it is generally desired to run the hydrolysis and condensation continuously. This makes it practical to run the process at greater dilutions and help increase the cyclic siloxane content of the product. In a continuous production scale reaction, the aqueous phase is recycled and depleted water is replenished so as to maintain a constant aqueous phase. In a continuous reactor the residence time is generally less than one minute, while at temperatures between 25°C. and 60°C. the preferred residence time can be less than ten seconds. In a batch reaction the residence time is considerably longer than in a continuous system and varies from minutes to hours.

While it is preferred to carry out the process of this invention in the absence of a solvent, conventional solvents can be employed if desired.

The cyclic siloxane products of this invention can be recovered from the aqueous phase by any conventional method heretofore employed in conventional hydrolysis and condensation reactions. Due to the lack of solubility of the cationic surface active agent in the cyclic siloxane product, the siloxane product phase normally need only be physically separated from the aqueous phase and washed with water. Of course, other conventional purification procedures can be applied to the cyclic siloxane product such as neutralization with sodium carbonate and the individual cyclic siloxanes (e.g. trimers, tetramers, etc.) separated by distillation if desired.

The cyclic siloxane compounds produced by the process of this invention have a wide variety of known uses e.g. they can be employed as additives in cosmetic formulations; as water repellants in the treatment of textiles and paper; as precursors for the production of silicone polymers such as gums, elastomers, fluids, surfactants, and the like; as well as in many other technical areas.

The following examples are illustrative of the present invention and are not to be regarded as limitative. It is to be understood that all parts, percentages and proportions referred to herein and in the appended claims are by weight unless otherwise indicated. Me in said examples represents a methyl radical. The bulk viscosity values given in said examples were determined by using Cannon-Fenske Routine Viscometers. The silanol content values given in said examples were determined by near infra red spectroscopy using known standards for absorbances.

EXAMPLE 1

To a stirred solution of 200 grams of aqueous hydrochloric acid (36.0–38.0 percent HCl) and 1.0 gram of n-octylamine in a 500 ml., 3-necked round bottom flask equipped with a bottom take-off, heating mantle, stirring system, addition funnel, "Y" tube, thermometer with adapter, Thermo-O-Watch and a Friedrich water condenser was added 129.0 grams (1 mole) of dichlorodimethylsilane over a 25 minute period at 29°C. ± 6°C. The reaction solution was then stirred for 5 more minutes following the addition of the silane. The reaction solution was then allowed to stand for thirty minutes to effect a clean phase separation after which the siloxane product phase was decanted from the aqueous phase. The siloxane product was then neutralized with damp sodium bicarbonate at 90°C. for 15 minutes. The siloxane product was then cooled and vacuum filtered. Vapor phase chromatographic analysis of the neutralized siloxane product filtrate showed 61.6% cyclic dimethylsiloxane tetramer 15.9% cyclic dimethylsiloxane pentamer and 1.9% cyclic dimethylsiloxane hexamer. The balance of said siloxane filtrate was essentially silanol terminated linear dimethylsiloxane. Said siloxane filtrate also had a bulk viscosity of 4.2 centistokes and a silanol content of 0.59%.

EXAMPLE 2

As a control experiment the procedure of Example 1 was repeated except that the n-octylamine additive was omitted. Vapor phase chromatographic analysis of the control neutralized siloxane product filtrate showed only 23–36% cyclic dimethylsiloxane tetramer, 8–9% of cyclic dimethylsiloxane pentamer, and 2% of cyclic dimethylsiloxane hexamer. The balance of said siloxane filtrate was essentially silanol terminated linear dimethylsiloxane.

EXAMPLE 3

The procedure of Example 1 was repeated except that 2.7 grams of n-hexylamine was used in place of n-octylamine. Vapor phase chromatographic analysis of the neutralized siloxane product filtrate showed 58.7% cyclic dimethylsiloxane tetramer, 15% cyclic dimethylsiloxane pentamer and 1.9% cyclic dimethylsiloxane hexamer. The balance of said siloxane filtrate was essentially silanol terminated linear dimethylsiloxane. Said siloxane filtrate also had a bulk viscosity of 5.6 centistokes and a silanol content of 0.93%.

EXAMPLE 4

The procedure of Example 1 was repeated except that the separated siloxane product was not neutralized and 1.0 grams of n-dodecylamine was used in place of n-octylamine. Vapor phase chromatographic analysis of the unneutralized siloxane product showed 53.3% cyclic dimethylsiloxane tetramer, 18.5% cyclic dimethylsiloxane pentamer and 3.6% cyclic dimethylsiloxane hexamer. The balance of said siloxane product was essentially chloro terminated linear dimethylsiloxane.

EXAMPLE 5

As a comparison experiment the procedure of Example 1 was repeated except that the separated siloxane product was not neutralized and 1.0 gram of n-butylamine was used in place of n-octylamine. Vapor phase chromatographic analysis of the unneutralized siloxane product showed 36.1% cyclic dimethylsiloxane tetramer, 8.8% cyclic dimethylsiloxane pentamer and 1.8% cyclic dimethylsiloxane hexamer. The balance of said siloxane product was essentially chloro terminated linear dimethylsiloxane. This is essentially the same result as can be expected from a control run which omits the n-butylamine precursor.

EXAMPLE 6

The procedure of Example 1 was repeated except that 3.4 grams of di-n-butylamine was used in place of n-octylamine. Vapor phase chromatographic analysis of the neutralized siloxane product filtrate showed 49.2% cyclic dimethylsiloxane tetramer, 12.3% cyclic dimethylsiloxane pentamer and 1.9% cyclic dimethylsiloxane hexamer. The balance of said siloxane filtrate was essentially silanol terminated linear dimethylsiloxane. Said siloxane filtrate also had a bulk viscosity of 6.8 centistokes and a silanol content of 0.56%.

EXAMPLE 7

The procedure of Example 1 was repeated except that 4.9 grams of tri-n-butylamine was used in place of n-octylamine. Vapor phase chromatographic analysis of the neutralized siloxane product filtrate showed 59.5% cyclic dimethylsiloxane tetramer, 14.5% cyclic dimethylsiloxane pentamer and 1.9% cyclic dimethylsiloxane hexamer. The balance of said siloxane filtrate was essentially silanol terminated linear dimethylsiloxane. Said siloxane filtrate also had a bulk viscosity of 4.4. centistokes and a silanol content of 0.78%.

EXAMPLE 8

The procedure of Example 1 was repeated except that 9.9 grams of tetra-n-butylammonium iodide was used in place of n-octylamine. Vapor phase chromatographic analysis of the neutralized siloxane product filtrate showed 64.4% cyclic dimethylsiloxane tetramer, 15.3% cyclic dimethylsiloxane pentamer and 1.8% cyclic dimethylsiloxane hexamer. The balance of said siloxane filtrate was essentially silanol terminated linear dimethylsiloxane. Said siloxane filtrate also had a bulk viscosity of 3.8 centistokes and a silanol content of 0.76%.

EXAMPLE 9

The procedure of Example 1 was repeated except that 2.4 grams of valeric acid was used in place of n-octylamine. Vapor phase chromatographic analysis of the neutralized siloxane product filtrate showed 52.9% cyclic dimethylsiloxane tetramer, 12.7% cyclic dimethylsiloxane pentamer and 2.1% cyclic dimethylsiloxane hexamer. The balance of said siloxane filtrate was essentially silanol terminated linear dimethylsiloxane. Said siloxane filtrate also had a bulk viscosity of 6.3 centistokes and a silanol content of 0.90%.

EXAMPLE 10

The procedure of Example 1 was repeated except that 2.4 grams of t-amyl alcohol was used in place of n-octylamine. Vapor phase chromatographic analysis of the neutralized siloxane product filtrate showed 50.2% cyclic dimethylsiloxane tetramer, 11.0% cyclic dimethylsiloxane pentamer and 1.8% cyclic dimethylsiloxane hexamer. The balance of said siloxane filtrate was essentially silanol terminated linear dimethylsiloxane. Said siloxane filtrate also had a bulk viscosity of 5.7 centistokes and a silanol content of 0.92%.

EXAMPLE 11

The procedure of Example 1 was repeated except this time a solution of 200 grams of aqueous hydrochloric acid (36.0–38.0 percent HCl) and 2.7 grams of n-hexylamine was added with stirring to 129.0 grams of dichlorodimethylsilane over a 25 minute period at a temperature range of 7°C. to 36°C. Vapor phase chromatographic analysis of the neutralized siloxane product filtrate showed 46.8% cyclic dimethylsiloxane tetramer, 10.9% cyclic dimethylsiloxane pentamer and 2.1% cyclic dimethylsiloxane hexamer. The balance of said siloxane filtrate was essentially silanol terminated linear dimethylsiloxane. Said siloxane filtrate also had a bulk viscosity of 8.1 centistokes and a silanol content of 1.0%.

EXAMPLE 12

As a control experiment the procedure of Example 11 was repeated except that the n-hexylamine additive was omitted. Vapor phase chromatographic analysis of the control neutralized siloxane product filtrate showed only 36.2% cyclic dimethylsiloxane tetramer, 8.6% cyclic dimethylsiloxane pentamer and 2.0% cyclic dimethylsiloxane hexamer. The balance of said siloxane filtrate was essentially silanol terminated linear dimethylsiloxane. Said siloxane filtrate also had a bulk viscosity of 14.7 centistokes and a silanol content of 0.95%.

EXAMPLE 13

The procedure of Example 1 was repeated except that 88.7 grams of linear 1,5-dichlorohexamethyltrisiloxane (90.9% purity) and 2.7 grams of n-hexylamine was used instead of dichlorodimethylsilane and n-octylamine. Said linear siloxane was added over a period of 18 minutes at a temperature of 27°C ± 3°C and the reaction solution was stirred for 12 additional minutes following the addition of the linear siloxane. Vapor phase chromatographic analysis of the neutralized siloxane product filtrate showed (after normalizing the analysis of the filtrate for impurities in the linear siloxane starting material) that the amount of cyclic siloxanes formed was 44.1% cyclic dimethylsiloxane tetramer, 9.9% cyclic dimethylsiloxane pentamer and 2.5% cyclic dimethylsiloxane hexamer. The balance of said siloxane filtrate was essentially silanol terminated linear dimethylsiloxane. Said siloxane filtrate also had a bulk viscosity of 6.3 centistokes and a silanol content of 0.93%.

EXAMPLE 14

As a control experiment Example 13 was repeated except that the n-hexylamine additive was omitted. Vapor phase chromatography showed that the normalized yields of the control neutralized siloxane product filtrate were only 23.8% cyclic dimethylsiloxane tetramer, 6.7% cyclic dimethylsiloxane pentamer and 2.5% cyclic dimethylsiloxane pentamer. The balance of said siloxane filtrate was essentially silanol terminated linear dimethylsiloxane. Said siloxane filtrate also had a bulk viscosity of 16.6 centistokes and a silanol content of 0.84%.

EXAMPLE 15

Using the same apparatus as in Example 1, to a stirred solution of 63.0 grams (3.5 moles) of distilled water and 3.0 grams of tetra-n-propylammonium chloride was added 74.0 grams of diethyoxydimethylsilane (about 95.0% purity) over a 28 minute period at 30°C ± 6°C. The siloxane product phase was separated from the aqueous phase, centrifuged, repeatedly washed with a saturated aqueous sodium chloride solution, decanted and vacuum filtered. Vapor phase chromatographic analysis of the treated siloxane product showed 2.9% unreacted diethoxydimethylsilane, 35.0% cyclic dimethylsiloxane tetramer and 5.0% cyclic dimethylsiloxane pentamer. The balance of said siloxane product was essentially ethoxy and silanol terminated linear dimethylsiloxanes. Said siloxane product also had a bulk viscosity of 5.9 centistokes and a silanol content of 1.93%.

EXAMPLE 16

As a control experiment Example 15 was repeated except that the tetra-n-propylammonium chloride additive was omitted. Vapor phase chromatographic analysis of the control treated siloxane product showed 3.4% unreacted diethoxydimethylsilane, 18.3% cyclic dimethylsiloxane tetramer and 2.9% cyclic dimethylsiloxane pentamer. The balance of said treated siloxane product was essentially ethoxy and silanol terminated linear dimethylsiloxanes. Said treated siloxane product also had a bulk viscosity of 5.8 centistokes and a silanol content of 2.6%.

EXAMPLE 17

The procedure of Example 1 was repeated except that a solution of 29.0 grams of dichloromethylsilane (about 0.25 mole, $\geq$ 99.5% purity) and 97.0 grams of dichlorodimethylsilane (about 0.75 mole, $\geq$ 99.0% purity) was added to a stirred solution of 200 grams of aqueous hydrochloric acid (36–38 percent HCl) and 2.7 grams of n-hexylamine over a 36 minute period at a temperature range of 5°C to 36°C. Vapor phase chromatographic analysis of the neutralized siloxane product filtrate showed 1.2% of a cyclic siloxane tetramer of the formula $(Me_2SiO)(MeHSiO)_3$, 3.1% of a cyclic siloxane tetramer of the formula $(Me_2SiO)_2(MeHSiO)_2$, 10.7% of a cyclic siloxane tetramer of the formula $(Me_2SiO)_3(MeHSiO)$, 22.2% of cyclic dimethylsiloxane tetramer and a cyclic siloxane pentamer of the formula $(Me_2SiO)(MeHSiO)_4$, 1.2% of a cyclic siloxane pentamer of the formula $(Me_2SiO)_2(MeHSiO)_3$, 2.0% of a cyclic siloxane pentamer of the formula $(Me_2SiO)_3(MeHSiO)_2$, 4.3% of a cyclic siloxane pentamer of the formula $(Me_2SiO)_4(MeHSiO)$ and 5.1% of cyclic dimethylsiloxane pentamer. The balance of said siloxane filtrate was essentially silanol terminated linear siloxanes. Said siloxane filtrate also had a bulk viscosity of 12.4 centistokes and a silanol content of 0.53%.

EXAMPLE 18

As a control experiment Example 17 was repeated except that the n-hexylamine additive was omitted. Vapor phase chromatographic analysis of the control neutralized siloxane product filtrate showed only 0.5% of a cyclic siloxane tetramer of the formula $(Me_2SiO)(MeHSiO)_3$, 1.9% of a cyclic siloxane tetramer of the formula $(Me_2SiO)_2(MeHSiO)_2$, 5.1% of a cyclic siloxane tetramer of the formula $(Me_2SiO)_3(MeHSiO)$, 9.6% of cyclic dimethylsiloxane tetramer and a cyclic siloxane pentamer of the formula $(Me_2SiO)(MeHSiO)_4$, 1.0% of a cyclic siloxane pentamer of the formula $(Me_2SiO)_2(MeHSiO)_3$, 1.4% of a cyclic siloxane pentamer of the formula $(Me_2SiO)_3(MeHSiO)_2$, 2.5% of a cyclic siloxane pentamer of the formula $(Me_2SiO)_4(MeHSiO)$ and 2.3% of cyclic dimethylsiloxane pentamer. The balance of said siloxane filtrate was essentially silanol terminated linear siloxanes. Said siloxane filtrate also had a bulk viscosity of 32.0 centistokes and a silanol content of 0.70%.

EXAMPLE 19

The procedure of Example 1 was repeated except that a solution composed of 48.0 grams of gamma-chloropropyldichloromethylsilane (about 0.25 mole, 98.6% purity) and 97.0 grams of dichlorodimethylsilane (0.75 mole, $\geq$ 99.0% purity) was added to a stirred solution of 200.0 grams of aqueous hydrochloric acid (36–38 percent HCl) and 2.7 grams of n-hexylamine over a 31 minute period at a temperature range of 9°C. to 34°C. Vapor phase chromatographic analysis of the neutralized siloxane product filtrate showed 11.8% cyclic dimethylsiloxane tetramer, 3.8% cyclic dimethylsiloxane pentamer, 1.5% of a cyclic trimer of the formula $(Me_2SiO)_2(Cl(CH_2)_3MeSiO)$, 0.4% cyclic dimethylsiloxane hexamer, 26.4% of a cyclic siloxane tetramer of the formula $(Me_2SiO)_3(Cl(CH_2)_3MeSiO)$, 6.2% of a cyclic siloxane pentamer of the formula $(Me_2SiO)_4(Cl(CH_2)_3MeSiO)$, 13.6% of a cyclic siloxane tetramer of the formula $(Me_2SiO)_2(Cl(CH_2)_3MeSiO)_2$, and 3.6% of a cyclic siloxane pentamer of the formula $(Me_2SiO)_3(Cl(CH_2)_3MeSiO)_2$ The balance of said siloxane filtrate was essentially silanol terminated linear siloxanes. Said siloxane filtrate also had a bulk viscosity of 10.2 centistokes and a silanol content of 0.74%.

EXAMPLE 20

As a control experiment Example 19 was repeated except that the n-hexylamine additive was omitted. Vapor phase chromatographic analysis of the control neutralized siloxane filtrate showed only 6.0% cyclic dimethylsiloxane tetramer, 1.7% cyclic dimethylsiloxane pentamer, 0.2% of a cyclic siloxane trimer of the formula $(Me_2SiO)_2(Cl(CH_2)_3MeSiO)$, 0.3% cyclic dimethylsiloxane hexamer, 15.9% of a cyclic siloxane tetramer of the formula $(Me_2SiO)_3(Cl(CH_2)_3MeSiO)$, 3.6% of a cyclic siloxane pentamer of the formula $(Me_2SiO)_4(Cl(CH_2)_3MeSiO)$, 7.7% of a cyclic siloxane tetramer of the formula $(Me_2SiO)_2(Cl(CH_2)_3MeSiO)_2$, and 2.5% of a cyclic siloxane pentamer of the formula $(Me_2SiO)_3(Cl(CH_2)_3MeSiO)_2$. The balance of said siloxane filtrate was essentially silanol terminated linear siloxanes. Said siloxane filtrate also had a bulk viscosity of 41.0 centistokes and a silanol content of 0.47%.

EXAMPLE 21

Dichlorodimethylsilane was hydrolyzed and condensed with a solution of concentrated aqueous hydrochloric acid containing 1.0 weight percent n-octylamine in a continuous reactor system. The reactor system consisted of two reactant entry ports to a common feed pipe where a stream of the aqueous-acid-amine medium was intimately mixed with a stream of the silane starting material. Said feed pipe was connected to a verticle reactor vessel through which the reaction medium was percolated by the gaseous hydrogen chloride by-product. In a gas-liquid separator connected to the top of said reactor vessel, the HCl gas was separated by sending it through a condenser which removed the volatilized by-product. The aqueous and siloxane product phases then flowed into a decanter from which the desired lighter siloxane product phase was allowed to over-flow and be collected. The aqueous phase was continuously recycled as it drained from the decanter by a pump through a heat exchanger which was used to maintain a constant reaction temperature back to the common feed pipe. Makeup water was added through the aqueous reactant entry port to maintain the desired level of water in the decanter. In the continuous hydrolysis and condensation reaction of this experiment the aqueous-acid-amine solution to silane flow rate was set at 16 parts by weight of said solution to one part by weight of said silane. The constant reaction temperature was 55°C and the average residence time of the reaction solution in the reactor vessel was 0.5 seconds. The desired siloxane product obtained upon continuous constant production was neutralized and vapor phase chromatographic analysis of said neutralized product showed 0.7% cyclic dimethylsiloxane trimer, 72.5% cyclic dimethylsiloxane tetramer, 15.8% cyclic dimethylsiloxane pentamer, 2.5% cyclic dimethylsiloxane hexamer and 0.5% cyclic dimethylsiloxane heptamer. The balance of said siloxane product was essentially silanol terminated linear siloxanes.

EXAMPLE 22

As a control experiment Example 21 was repeated except that the n-octylamine additive was omitted. Vapor phase chromatographic analysis of the control neutralized siloxane product showed only a total of 49.6% for all of the cyclic dimethylsiloxane compounds produced. The balance of said siloxane product was essentially silanol terminated linear siloxanes.

Various modifications and variations of this invention will be obvious to a worker skilled in the art and it is to be understood that such modifications and variations are to be included within the purview of this application and the spirit and scope of the appended claims.

What is claimed is:

1. In a process for preparing cyclic siloxane compounds, said process consisting essentially of the hydrolysis and condensation of a hydrolyzable organosilicon compound, the improvement comprising increasing the yield of said cyclic siloxane compounds by hydrolyzing and condensing said organosilicon compound in the presence of a cationic surface active agent, said agent being essentially soluble only in the aqueous phase of said process, wherein the concentration of the cationic surface active agent in said aqueous phase is from about 0.01 to about 10 weight percent, wherein said cationic surface active agent is selected from the class consisting of a salt of a protonated amine, a quaternary ammonium salt, a salt of a protonated carboxylic acid, a salt of a protonated alcohol, a salt of a protonated nitrile, a salt of a protonated sulfoxide, a salt of a protonated mercaptan, a quaternary phosphonium salt, and a salt of a protonated phosphine, wherein the cation of each salt contains from 5 to 30 carbon atoms, and wherein the anion of each salt is selected from the group consisting of halide, sulfate, and phosphate anions.

2. A process as defined in claim 1 wherein said process is carried out in the absence of a solvent and wherein the cationic surface active agent is a salt of a protonated amine and wherein the anion of said salt is a chloride anion.

3. A process as defined in claim 2 wherein the concentration of the cationic surface active agent in said aqueous phase is from about 0.5 to about 2 weight percent.

4. A process as defined in claim 2 wherein the cationic surface active agent is formed in situ by employing an aqueous phase that contains hydrochloric acid and a precursor amine selected from the class consisting of primary amines of the formula $RNH_2$ wherein R is a monovalent hydrocarbon radical having 6 to 10 carbon atoms, secondary amines of the formula $R_2NH$ wherein R is a monovalent hydrocarbon radical wherein the sum number of the carbon atoms of both R radicals of the secondary amine ranges from 6 to 14; and tertiary amines of the formula $R_3N$ wherein R is a monovalent hydrocarbon radical wherein the sum number of the carbon atoms of all three R radicals of the tertiary amine ranges from 9 to 18.

5. A process as defined in claim 4 wherein R is an n-alkyl radical.

6. A process as defined in claim 5 wherein the cationic surface active agent is a primary amine.

7. A process as defined in claim 6 wherein the primary amine is n-octylamine.

8. A process as defined in claim 4 that is carried out in a continuous manner.

9. A process as defined in claim 2 wherein the hydrolyzable organosilicon compound is selected from the class consisting of silanes of the formula $$R_nSi-X_{4-n}$$

wherein R represents a radical selected from the class consisting of hydrogen and a monovalent hydrocarbon radical $n$ has a value of 0 to 3 and X is a hydrolyzable group; siloxanes of the formula $$(X)R_2SiO(R_2SiO)_xSiR_2(X)$$

wherein R and X are the same as defined above and $x$ has a value of 0 to 3; and silylamines of the formula $$(X)R_2SiN(R_2SiN)_xSiR_2(X) \quad \overset{R}{} \quad \overset{R}{}$$

wherein R, X and $x$ are the same as defined above.

10. A process as defined in claim 4 wherein the hydrolyzable organosilicon compound is a silane of the formula $$R_n-Si-X_{4-n}$$

wherein R represents a radical selected from the class consisting of hydrogen and a monovalent hydrocarbon radical, $n$ has a value of 0 to 3 and X is a hydrolyzable group.

11. A process as defined in claim 10, wherein R is methyl, $n$ is 2 and X is a chlorine radical.

12. A process as defined in claim 5, wherein the hydrolyzable organosilicon compound is selected from the class consisting of dichlorodimethylsilane, a mixture of dichlorodimethylsilane and dichloromethylsilane, and a mixture of dichlorodimethylsilane, dichloromethylsilane and chlorotrimethylsilane.

13. A process as defined in claim 7 wherein the hydrolyzable organosilicon compound is dichlorodimethylsilane.

* * * * *